(12) United States Patent
Benoit et al.

(10) Patent No.: US 9,546,965 B2
(45) Date of Patent: *Jan. 17, 2017

(54) AUTOMATED WOOD SPECIES IDENTIFICATION

(71) Applicant: USNR, LLC, Woodland, WA (US)

(72) Inventors: Ghislain Benoit, Salmon Arm (CA);
David Liebich, Salmon Arm (CA);
Harry Ogloff, Salmon Arm (CA)

(73) Assignee: USNR, LLC, Woodland, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/713,852

(22) Filed: May 15, 2015

(65) Prior Publication Data

US 2015/0285747 A1   Oct. 8, 2015

Related U.S. Application Data

(63) Continuation of application No. 13/243,256, filed on Sep. 23, 2011, now Pat. No. 9,063,094.

(60) Provisional application No. 61/386,332, filed on Sep. 24, 2010.

(51) Int. Cl.
*G01N 21/898* (2006.01)
*G01N 33/46* (2006.01)
*H04N 7/18* (2006.01)

(52) U.S. Cl.
CPC ........ *G01N 21/8986* (2013.01); *G01N 21/898* (2013.01); *G01N 33/46* (2013.01); *H04N 7/183* (2013.01)

(58) Field of Classification Search
None
See application file for complete search history.

(56) References Cited

U.S. PATENT DOCUMENTS

| 5,071,771 A | 12/1991 | Barbour et al. |
| 6,624,883 B1 | 9/2003 | Zhou |
| 7,324,904 B2 | 1/2008 | Floyd et al. |
| 7,603,904 B2 | 10/2009 | Harris |

(Continued)

FOREIGN PATENT DOCUMENTS

| JP | H07-146236 A | 6/1995 |
| JP | 2005-214924 A | 8/2005 |

(Continued)

OTHER PUBLICATIONS

Meier, E., "Wood Identification Guide," the Wood Database (retrieved Feb. 10, 2014), http://www.wooddatabase.com/wood-articles/wood-identification-guide, Sep. 4, 2009 as per Wayback Machine.

(Continued)

*Primary Examiner* — Peter D Le
(74) *Attorney, Agent, or Firm* — Schwabe Williamson & Wyatt

(57) ABSTRACT

Embodiments provide methods, apparatuses, and systems for identification of wood species based on one or more pitch characteristics. A workpiece may be exposed to a beam of radiation from a radiation source. The beam of radiation may cause pitch on or within the workpiece to emit visible light. The emitted light may be imaged and used to determine pitch content, pitch location. a pitch deposition pattern, pitch emission wavelength, and/or other characteristics of the workpiece. One or more of these characteristics may be used to identify a tree species or group of tree species from which the workpiece was cut or manufactured.

14 Claims, 11 Drawing Sheets

(56) References Cited

U.S. PATENT DOCUMENTS

| | | |
|---|---|---|
| 7,751,612 B2 | 7/2010 | Baker et al. |
| 2002/0074559 A1 | 6/2002 | Dowling et al. |
| 2003/0042180 A1 | 3/2003 | Kairi |
| 2004/0030536 A1 | 2/2004 | Woods et al. |
| 2005/0072935 A1 | 4/2005 | Lussier |
| 2006/0056659 A1 | 3/2006 | Laurent et al. |
| 2006/0267054 A1 | 11/2006 | Martin et al. |
| 2007/0137323 A1 | 6/2007 | Floyd |
| 2008/0043217 A1 | 2/2008 | Lundgren et al. |
| 2008/0074653 A1 | 3/2008 | Taylor |
| 2009/0100974 A1 | 4/2009 | Sawyer et al. |
| 2009/0179162 A1 | 7/2009 | Johnson |
| 2010/0132900 A1 | 6/2010 | Andersson et al. |
| 2010/0213063 A1 | 8/2010 | Zenhausern et al. |

FOREIGN PATENT DOCUMENTS

| | | |
|---|---|---|
| JP | 2007-171195 A | 7/2007 |
| JP | 2001-283281 A | 10/2012 |

OTHER PUBLICATIONS

PCT International Search Report and Written Opinion for PCT/US2011/053059, mailed Apr. 24, 2012.

Australian Examination Report No. 1 from the Australian Patent Office for AU2011305220, mailed Feb. 14, 2014.

US Office Action for U.S. Appl. No. 13/243,256, mailed Nov. 12, 2014.

First Examiner's Report from the New Zealand Intellectual Property Office for NZ Patent Application 609625, dated Oct. 21, 2013.

Second Examiner's Report from the New Zealand Intellectual Property Office for NZ Patent Application 609625, dated Feb. 5, 2015.

Examiner's Report from the Canadian Intellectual Property Office for CA Pat. No. 2,753,502, dated May 27, 2013.

US Notice of Allowance for U.S. Appl. No. 13/243,256, mailed Mar. 31, 2015.

Japanese Official Action for 2013-530367, mailed Jun. 12, 2015 (with English translation).

AUTOMATED WOOD SPECIES IDENTIFICATION

CROSS-REFERENCE TO RELATED APPLICATIONS

The present application is a continuation of U.S. application Ser. No. 13/243,256, filed Sep. 23, 2011, which claims the benefit of U.S. Provisional Patent Application No. 61/386,332, filed Sep. 24, 2010, the entire disclosures of which are hereby incorporated by reference.

TECHNICAL FIELD

Embodiments herein relate to the field of wood species identification, and, more specifically, to automated methods, systems, and apparatuses for identifying and/or differentiating among wood species.

BACKGROUND

Modern lumber manufacturing facilities often will process wood from a variety of tree species. Stems of wood, logs, cants, flitches, boards, and other workpieces may be sorted based on the species or type of tree from which the workpiece is derived. The determination of wood species typically requires visual inspection of the workpiece and determination of the wood species by a human operator.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
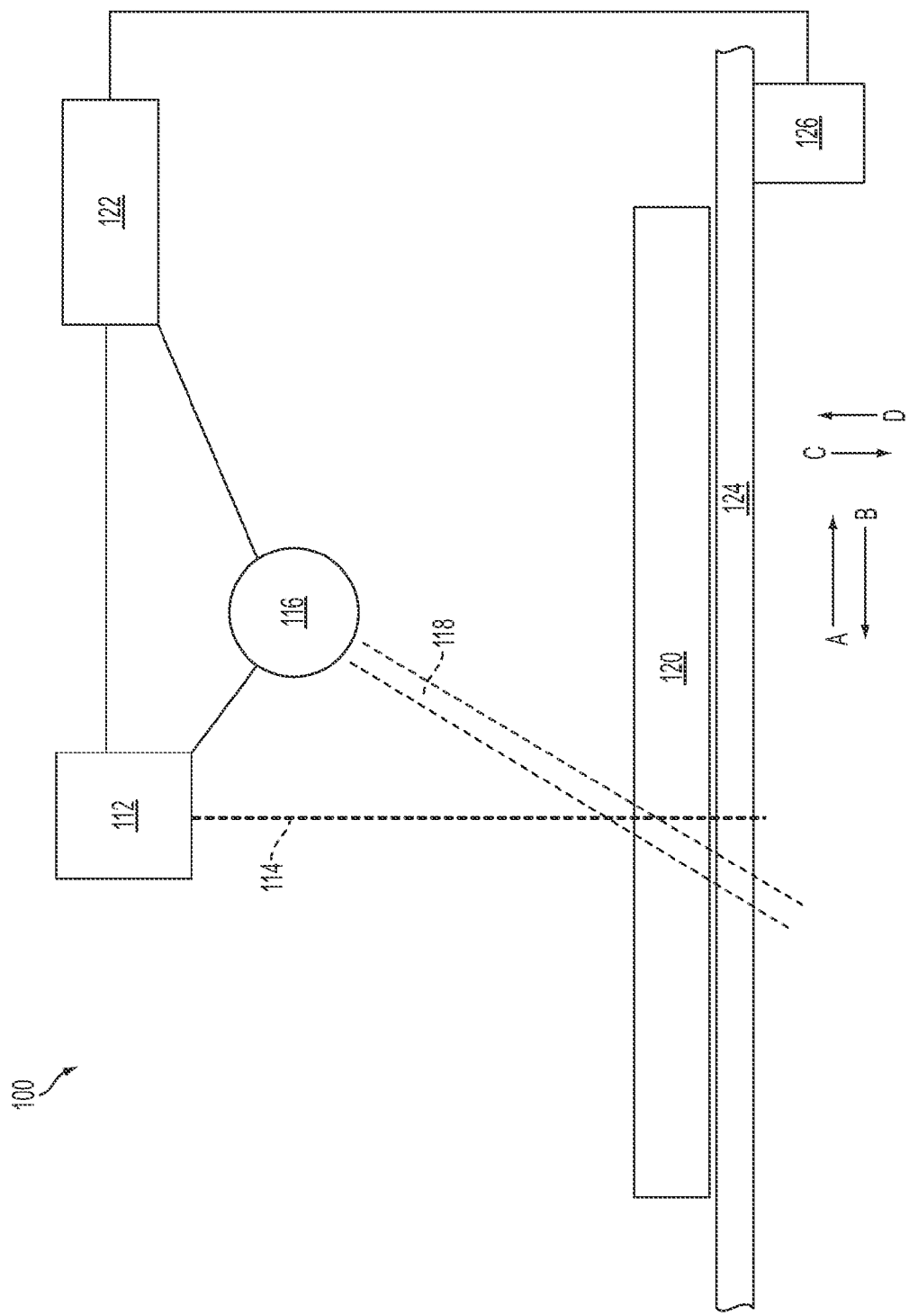
FIG. 1 shows a block diagram of a species identification system 100 in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods, apparatuses, and systems are provided for automated identification of wood species based on one or more pitch characteristics. In exemplary embodiments, a computing device may include one or more components of the disclosed apparatuses and/or systems and may be employed to perform one or more methods as disclosed herein.

As provided herein, a workpiece may be exposed to a beam of radiation from a radiation source. The beam of radiation may cause pitch on or within the workpiece to fluoresce. The fluorescence characteristics of the workpiece may be detected and/or measured and used to determine pitch content, pitch location. a pitch deposition pattern, pitch emission wavelength, and/or other characteristics of the workpiece. One or more of these characteristics may be used to identify a wood species or group of species from which the workpiece was cut or manufactured.

In some examples, one or more pitch characteristics may be used to distinguish workpieces of one wood species (e.g., "pine") from workpieces of one or more other wood species (e.g., spruce and fir) that may be similar in appearance. In other examples, pitch characteristics may be used to identify wood species such as pine, spruce, larch, maple, fir, cypress, hemlock, balsam, birch, hickory, walnut, alder, oak, cherry, cedar, mahogany, cottonwood, aspen, poplar, and/or elm.

As used herein, the term "workpiece" refers to a unit of wood or wood-based product. Examples of workpieces include but are not limited to boards, flitches, cants, stems, veneers, and engineered/composite materials derived from wood (e.g., particleboard, waferboard, plywood, fiberboard, and other engineered wood materials known in the art).

As used herein, the term "wood species" refers to a type or category of tree from which a workpiece was cut, manufactured, or at least partially derived. A wood species may include one, two, three or more tree species within a single taxonomic group such as a family, subfamily, or genus. Likewise, a wood species may include one, two, three or more sub-species or varieties within a single taxonomic species. As an example, three wood species may be "pine," "spruce," and "fir," any or all of which may include multiple tree species or varieties, and the wood species "pine", for example, may include some or all of the pine species found in North America, including, but not limited to Yellow Pine, Ponderosa Pine, Jeffery Pine, Shortleaf Pine, Bull Pine, Jack Pine, and/or White Pine.

Alternatively, a wood species may encompass one or more tree species, subspecies, or varieties grouped according to one or more common characteristics, such as pitch content, pitch location, pitch deposition pattern, wood color/tone, density, strength/stiffness, relative monetary value, hardness/softness, etc. For example, a single wood species encompassing tree species with a pitch content within a predetermined range or exceeding a predetermined threshold may include species of pine, spruce, and/or fir. Alternatively, a single wood species encompassing tree species with similar wood density and/or strength may include Douglas fir and larch. In another example, a single wood species may encompass one or more tree species having similar pitch deposition patterns.

As used herein, the term "pitch" refers collectively to any one or all of pitch, resin, resinous deposits, and/or sap.

FIG. 1 shows a block diagram of a species identification system 100 in accordance with various embodiments. In the illustrated example, species identification system 100 includes an imaging module 112, a radiation source 116, and a processing module 122. Also shown are a workpiece 120 positioned on a transport surface 124, which is operatively coupled to a transport driver 126. Processing module 122 may be operatively coupled to any or all of imaging module 112, radiation source 116, transport surface 124, and/or controller 126.

In operation, transport surface 124 may be driven by controller 126 to bring workpiece 120 into the line of sight 114 of imaging module 112. Radiation source 116 emits a radiation beam 118 (e.g. UV Light) toward workpiece 120. Pitch on/within workpiece 118 absorbs energy from radiation beam 118, causing excitation of atoms in the pitch. The pitch reemits energy as visible light (i.e., fluorescence).

Imaging module 112 captures one or more images of workpiece 120 as the pitch is fluorescing. Imaging module 112 sends the image data to processing module 122. Processing module 122 assembles the received image data into an image of the workpiece or some portion thereof. The assembled image is then analyzed to determine one or more pitch characteristics such as pitch content, pitch location, a pattern of pitch deposition, and/or pitch fluorescence wavelength(s).

Processing module 122 may use the determined pitch characteristic(s) to identify the wood species of the workpiece. As provided above, identifying the wood species may include identifying a particular genus, species, sub-species, or variety of tree from which the workpiece was cut/derived. Alternatively, the determined characteristic(s) may be used to identify a larger group of tree species from which the workpiece was cut/derived. In some examples, the determined characteristic(s) may be used to eliminate one or more species of tree as possible species from which the workpiece may have been cut (e.g., to determine that the workpiece was or was not cut/derived from a pine tree).

Imaging module 112 may be any device configured to capture an image of a workpiece by converting an optical image to an electric signal. In some embodiments, imaging module 112 may include a sensor having one or more pixelated metal oxide semiconductors. Suitable sensors include, but are not limited to, a charge-coupled device (CCD) image sensor, an electron multiplying CCD (EM-CCD) imager, an active-pixel sensor (APS) imager (e.g., a complementary metal-oxide-semiconductor (CMOS) APS imager), and/or a hybrid CCD/CMOS imager (e.g., a sCMOS imager with CMOS readout integrated circuits coupled to a CCD imaging substrate).

Imaging module 112 and/or one or more sensors therein may also include one or more shuttering mechanisms, such as a mechanical shutter or shutter transistors. For example, a sensor may be a line-scan CMOS imager with shutter transistors positioned adjacent to the active area of each pixel. In another example, a sensor may be an area-scan CMOS imager with a rolling shutter that exposes different lines of the array at different times. Alternatively, a sensor may be an area-scan CMOS imager with uniform synchronous shutter that exposes each pixel of the array simultaneously.

Imaging module 112 may further include additional components known in the art for use with imaging sensors, such as a circuit board (e.g., a printed circuit board), a lens, a power source, a processor, a memory/storage, a data transfer module (e.g., a wireless transmitter/transceiver, wired connector, etc.), an outer case, and/or one or more mounting elements configured to retain imaging module 112 on or against a support.

Imaging module 112 may include one or more filters, such as an optical anti-aliasing filter, Bayer filter/filter mosaic, or other optical filter known in the art. In some embodiments, at least one filter may be configured to admit visible light and to exclude UV light. In other embodiments, at least one filter may be configured to exclude UV light and some portion of the visible light spectrum (e.g. wavelengths of 380-475 nm, 590-750 nm, violet light, blue light, red/orange light, etc.). In some examples, a filter may be configured to admit only light within a particular range of wavelengths, such as 450-620 nm, 476-590 nm, or 490-580 nm). Therefore, imaging module 112 may create image data based on the full visible spectrum of light or only a portion thereof.

Imaging module 112 may capture successive images of the workpiece in sections as the workpiece is transported on transport surface 124. For example, imaging module 112 may capture successive line images extending across the workpiece transverse to the direction of flow. Imaging module 112 may send the image data to processor 122 as the image data is created (e.g., line by line). Alternatively, imaging module 112 may compile or buffer the image data until the workpiece has passed the imaging module's field of view, sending the collection of image data to processor 122 after the entire workpiece has been imaged. In some embodiments, processor 122 and imaging module 112 are included within an integrated device, while in other embodiments the image data may be transmitted wirelessly or through a wired connection.

Radiation source 116 may be any source of electromagnetic radiation configured to emit a beam of electromagnetic radiation toward a target. Radiation source 116 may include one or more sources of visible or non-visible light, including but not limited to light-emitting diodes (LEDs), lamps/bulbs, lasers, or other light sources known in the art. For example, radiation source 116 may include one, two, three, four or more linear arrays of LEDs that emit ultraviolet (UV) radiation. Radiation source 116 may also include a support medium coupling element configured to attach radiation source 116 (or some portion thereof) to imaging module 112 or to a wall, ceiling, or support surface. One or more light sources and/or arrays may be coupled to a timing control feature configured to strobe or pulse the emitted light. The timing control feature may also be coupled to processing module 122 and/or imaging module 112 to synchronize the pulsing of emitted light with image capture.

Radiation source 116 may be positioned above transport surface 124. Light sources within radiation source 116 may be arranged to extend across the transport surface, generally transverse to the direction of flow. In some examples, radiation source 116 may be mounted to or positioned within imaging module 112 and/or processing module 122. In various embodiments, radiation source 116 may be positioned to emit beams of radiation downwardly onto transport surface 124 at an angle of 0° (perpendicular to transport surface 124), −5° to 5°, −15° to 15°, −30° to 30°, −45° to 45° or −50° to 50°. Similarly, imaging module 112 may be positioned vertically above transport surface 124 and at an angle of 0° (perpendicular to transport surface 124), −5° to 5°, −15° to 15°, −30° to 30°, or −50° to 50°. Yet in various embodiments, the imaging module may be maintained at an angle with respect to the radiation source, which in some embodiments may be adjustable. In various embodiments, the angle between the imaging module 112 and the radiation source 116 may be between 2° and 50°

The relative angles of radiation source 116 and imaging module 112 may be adjusted such that the field of view intersects with the beams of radiation emitted by radiation source 116 at any vertical distance above the upper surface of transport surface 124. The adjustment may be made manually or automatically (e.g., by an actuator in response to a command received from processing module 122) to accommodate varying workpiece dimensions such as thickness. Alternatively, transport surface 124 may be manually or automatically adjusted upward and downward to accommodate varying workpiece dimensions. Transport speed may also be adjusted manually or automatically in accordance with the relative angles of radiation source 116 and imaging module 112. For example, as the angle of radiation source 116 (relative to vertical) decreases (e.g., from −30° to −14°, thereby increasing the intensity of emitted light at the workpiece, transport speed may be also be increased. As the angle of imaging module 112 increases, thereby enlarging the field of view, transport speed may be decreased. Controller 126 may calculate/adjust transport speed/position in response to a command from processing module 122.

Processing module 122 may be any type of computing processor known in the art, including but not limited to a central processing unit, a microprocessor, a graphics processing unit, a digital signal processor, and/or a coprocessor. Processing module 122 may include hardware, software, or a combination of hardware and software. In some embodiments, processing module 122 may be a processing unit of a computing apparatus such as a personal computer. In other embodiments, processing module 122 may be integrated within another system element such as radiation source 116, imaging module 112, and/or controller 126.

Processing module 122 may include imaging software, wood species reference data, and/or a species determination algorithm for the determination of wood species based on an input of received image data. The wood species reference data may include reference values that represent a 'signature profile' for one or more wood species. For example, the 'signature profile' of a wood species "pine" may include a pitch content exceeding a predetermined threshold, a pitch fluorescence wavelength of 495-505 nm, and a streaked pitch deposition pattern.

Processing module 122 may also include executable instructions operable, when executed, to assemble the received image data into a full or partial image of a workpiece and to analyze the assembled image to determine one or more characteristics such as pitch content, pitch location, a pattern of pitch deposition, and/or pitch fluorescence wavelength. The executable instructions may be further operable, when executed, to retrieve the species determination algorithm and/or wood species reference data from a local or remote storage/database and to identify the wood species of the workpiece by feeding the characteristic(s) into the algorithm and/or comparing the characteristic(s) to the wood species reference data.

Processing module 122 may input determined pitch content and pitch fluorescence wavelength into the algorithm to determine the wood species. Alternatively, processing module 122 may compare determined pitch characteristics to the wood species reference data to determine the wood species of the workpiece. In some embodiments, processing module 122 may use the algorithm to determine a possible wood species and may use the reference wood species data to confirm or verify the identification (or vice versa).

Processing module 122 may also be configured to generate sorting data and/or grading data based on the species determination. Processing module 122 may communicate sorting data or commands to another component of a wood processing system, such as a drop-out mechanism, mechanical sorter, workpiece marking device, or other processor to effectuate sorting or grading of the workpiece. Different sorting or grading rules may be applied to workpieces based on wood species determination. For example, a first set of grading rules may be used for workpieces determined to be of the wood species "pine" and a second set of grading rules may be used for workpieces determined to be of another wood species (e.g., fir or spruce). Grading rules may be applied by processing module 122 to generate grading data and/or commands, which may be sent to another component of the wood processing system as described above.

Processing module 122 may communicate a wood species determination, image data, an assembled image of a workpiece, one or more determined pitch characteristics, and/or other data to another processor (e.g., a scanner/optimizer) or other wood processing system component for use in one or more of defect detection, strength/stiffness prediction, grading, sorting, workpiece imaging, or any other process.

Controller 126 and transport surface 124 may include any combination of elements known in the art for use in transporting workpieces. For example, transport surface 124 may include a lugged chain, belt, or other conveyor surface. Controller 126 may be configured to drive or otherwise control movement of the lugged chain or belt. For example, controller 126 may include a motor operatively coupled to transport surface 124 and may be configured to drive movement of transport surface 124 in a direction of work flow (indicated by Arrow A), in a direction opposite to the direction of work flow (Arrow B), vertically downward (Arrow C), vertically upward (Arrow D), and/or laterally. In some embodiments, controller 126 may be a computing device and/or processor configured to control the operation of, and/or receive data from, any other component of species identification system 100 and/or one or more components of a workpiece feed path system. Examples of such components may include a scanner/optimizer, a variable speed drive, a fixed speed drive, a sorting apparatus, a drop-out apparatus, a workpiece positioner configured to flip, turn, or rotate a workpiece, a camera/imaging module positioner, a cutting device, a light or light array, an imager, a workpiece marking apparatus, and/or a conveyor.

The number and arrangement of the illustrated components may vary among embodiments. Alternative embodiments may include two, three, four, five or more imaging modules 112 and/or radiation sources 116. In some embodiments, one or more imaging modules 112 and radiation sources 116 may be positioned below transport surface 124 and configured to capture an image of the bottom surface of workpiece 120. Likewise, one or more imaging modules 112 and radiation sources 116 may be positioned along or proximal to one or both sides of transport surface 124 and angled to target the top, bottom, or one or more sides of workpiece 120.

In some examples, two or more imaging modules 112 may be arranged to provide occlusionless imaging of workpieces as described in U.S. Pat. No. 7,751,612, which is hereby incorporated by reference in its entirety. Briefly, the imaging modules 112 may have fields of view that overlap and/or are partially obstructed by transport surface 124, a frame, a support, or any other component of a wood processing system. The imaging modules 112 may image the bottom, top, and/or sides of the workpiece as described above, sending image data to the processing module 122. Processing module 122 may combine the image data from the imaging modules to obtain a complete and unobstructed image of the workpiece.

Figure 2:
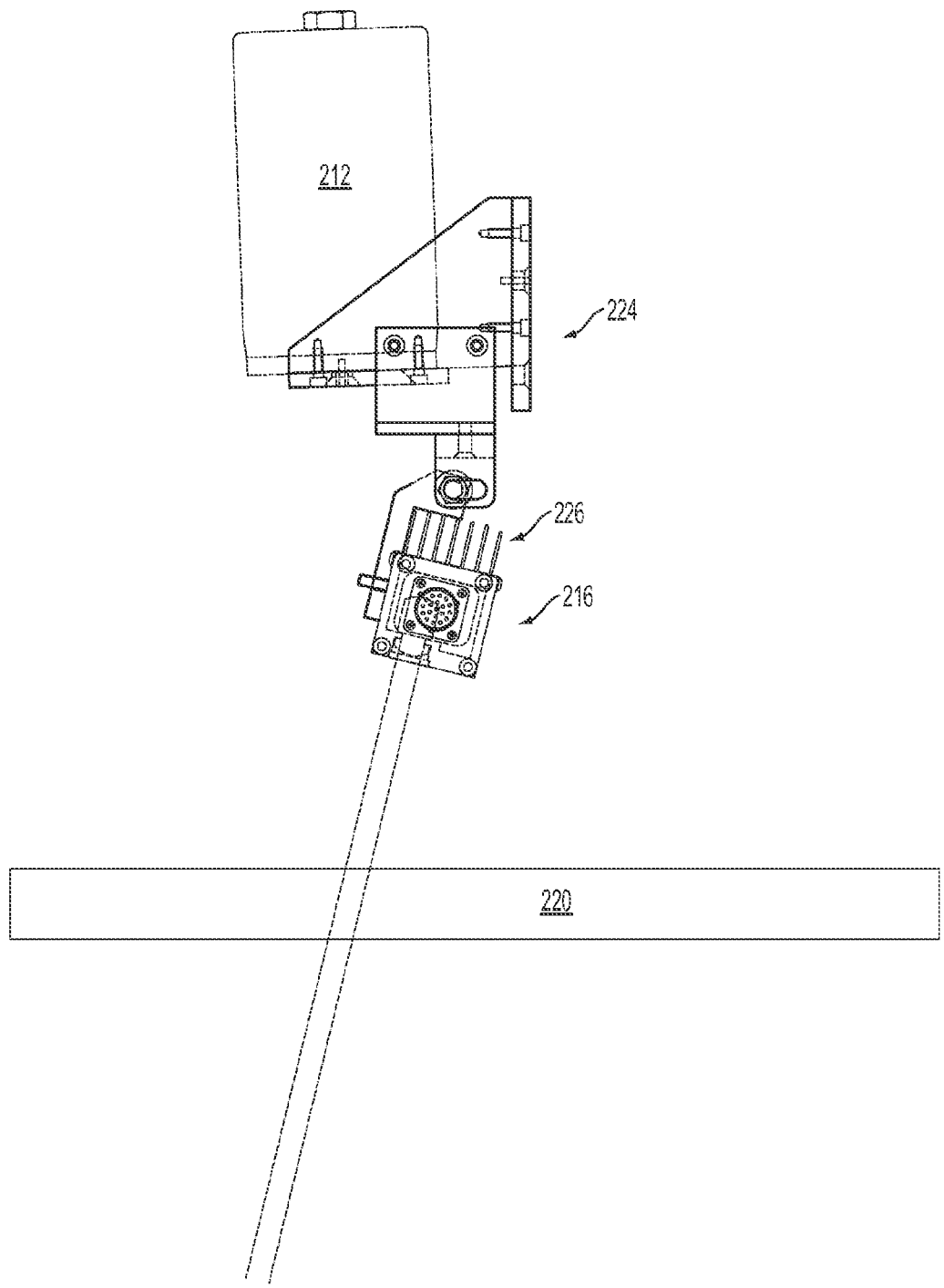
FIG. 2 illustrates an example of a radiation source and imaging module configuration for use to practice various embodiments.

FIG. 2 illustrates an example of a radiation source and imaging module configuration, in accordance with the above-described embodiments. The illustrated configuration may be provided as a component of a wood processing system or added to an existing wood processing system (e.g., added to an existing lumber transport in a sawmill facility).

An imaging module 212 and radiation source 216 are shown positioned in proximity to a workpiece 220. In the example of FIG. 2, imaging module 212 includes a CMOS array camera (1536×512 pixels, monochrome) with a 8 mm F1.4 lens, a 12 VDC to 24 VDC power supply, and a 10.5" (+/−1.5") sensor standoff. The CMOS array camera is contained within a sealed sensor package. Additional details of imaging module 212 are provided in FIGS. 3a-3d and identified in the accompanying Chart 1, below.

CHART 1

| MK | QTY | DESCRIPTION |
|---|---|---|
| 231 | 1 | GASKET-ENCLOSURE |
| 232 | 8 | CAPSCREW 8-32X¾ SKT HD |
| 233 | 2 | RETAINING CAP LASER |
| 234 | 2 | ALIGNMENT BALL LASER |
| 235 | 1 | MOUNT-CAMERA ARRAY |
| 236 | 2 | NUT JAM ⅝" SS ¼" THICK |
| 237 | 2 | SENSOR RET. BOLT |
| 238 | 2 | O RING 3-32X⁹⁄₁₆ (#113) |
| 239 | 1 | HOLDER METHODE |
| 240 | 6 | CAPSCREW 10-32X½ SKT HD FL |
| 241 | 4 | CAPSCREW 10-32X1 |
|  | 1 | CLAY DESICCANT ACT ½ OZ UNIT |
|  | 1 | SHIPPING BOX LPL/VISION SENSOR |
|  | 2 | SENSOR FOAM LPL/VISION SENSOR |
| 242 | 4 | CAPSCREW 10-32X½ SKT HD |
| 243 | 8 | LOCK WASHER ³⁄₁₆ #10 |
| 244 | 4 | CAPSCREW 10-32X1 SKT HD |
|  | 2 | CAPSCREW M2X5MM SKT HD |
| 245 | 1 | VISION, W2-BK7 5.928X1.938-658 |
| 246 | 2 | CAPSCREW 2-56X½ SKT HD |
| 247 | 8 | LOCK WASHER #8 |
| 248 | 4 | CAPSCREW 6-32X¼ SKT HD |
| 249 | 1 | FACEPLATE-VISION SENSOR |
| 250 | 2 | MOUNT, LASER SPLIT BALL, VISION |
| 251 | 1 | CONNECTOR BLOCK |
| 252 | 1 | GASKET-CONNECTOR |
| 253 | 1 | SUPPORT-CAMERA 2 |
| 254 | 1 | SUPPORT-CAMERA 1 |

CHART 1-continued

| MK | QTY | DESCRIPTION |
|---|---|---|
| 255 | 1 | CAN-VISION SENSOR |
|  | 4 | CAPSCREW 4-40X⅝ SKT HD |
|  | 4 | CAPSCREW 4-40X½ SKT HD |
| 256 | 1 | CONN S16/19C REV RECP PIN SL'D |
| 257 | 20 | CONN PIN GOLDFLASH 24-28 AWG |
| 258 | 1 | NKK PB GRN MOM NON-ILLUM |
| 259 | 1 | CONN FBR SC-SC DUPLEX BULKHEAD |
|  | 1 | CONN DB9 SHELL-SLIM |
|  | 1 | CAP .1 UF X7R 50 V 10% 1 LS TAPE |
|  | 1 | CAP 10 UF 16 V TANT .1 SP |
|  | 1 | CONN DB9S SLDR CUP |
|  | 1 | FIBREOPTIC TRANSCEIVER |
|  | 1 | CABLE FIBRE 8" SC/SC DUPLEX |
|  | 1 | VISION, W2-BK7 5.928X1.938-658 |
|  | 1 | LENS 17 MM F 1.4 COMPACT |
|  | 1 | SHIM .062" 1" I.D. × 1.5" O.D. |
|  | 1 | CAMERA RANGER M50 OEM-1 |
| 260 | 1 | LASER 830 NM 100 MW 59 DOT LINE |
| 261 | 1 | LASER 660 NM 50 MW 45 DEG EXTPOT |
|  | 1 | CD CASE SLIMLINE SINGLE |
|  | 1 | CD MEDIA 16X 74 M 650 MB |
|  | 1 | CAP 220 UF 16 V ELECT .1 SP |
|  | 1 | SOCKET T0-3 .090 BOSS HEIGHT |
|  | 1 | INSULATOR T0-3 1.625 X 1.093 |
|  | 1 | VOLTAGE REGULATOR T03 CASE |
|  | 2 | CONN DB SCRWLCK 4-40X0.312 |
|  | 4 | WASHER FLAT SPAENAUR |
| 262 | 1 | CONN FBR SC-SC DUPLEX DUST CAP |
|  | 1 | METER HOUR CURTIS LCD 12-48 VDC |
| 263 | 1 | GASKET 1⁹⁄₁₆ OD X 1³⁄₁₆ ID |

Figure 3A:
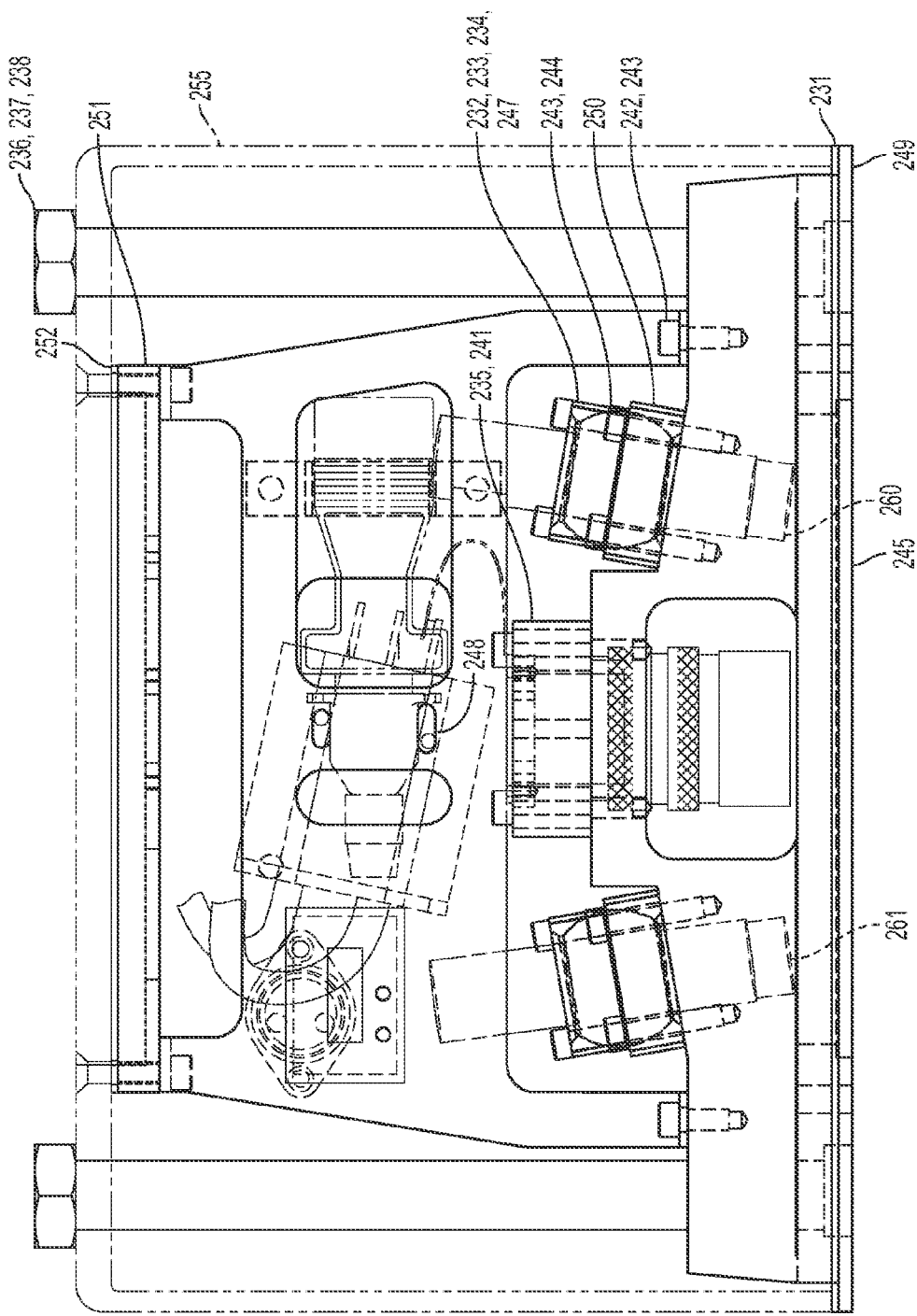
FIGS. 3a-3d illustrate the imaging module of FIG. 2 in accordance with various embodiments.
Figure 3B:
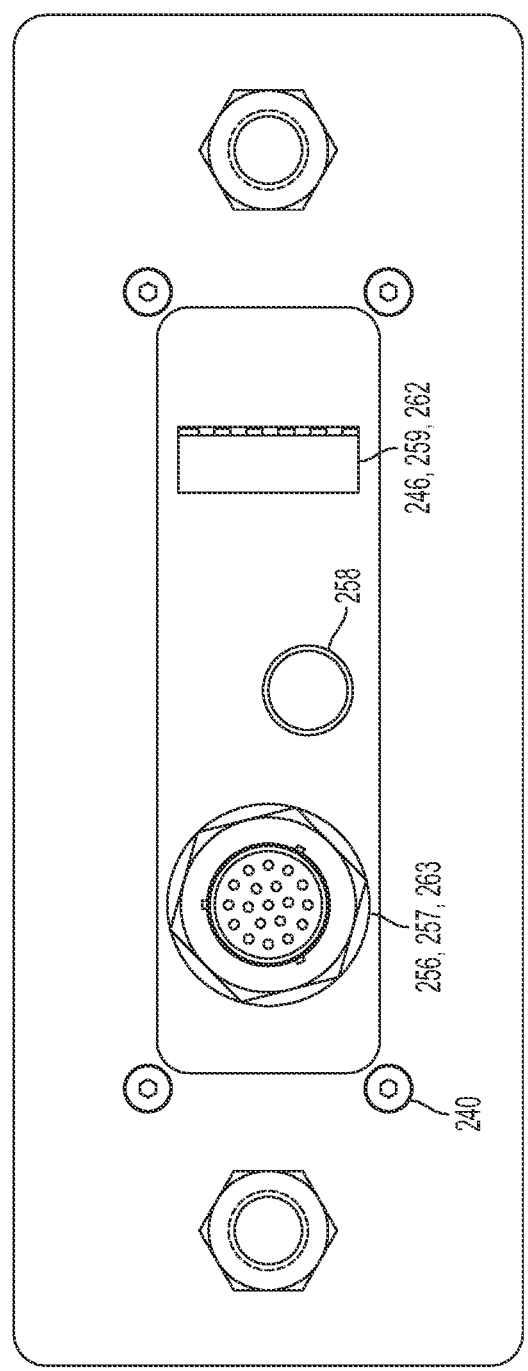
Figure 3C:
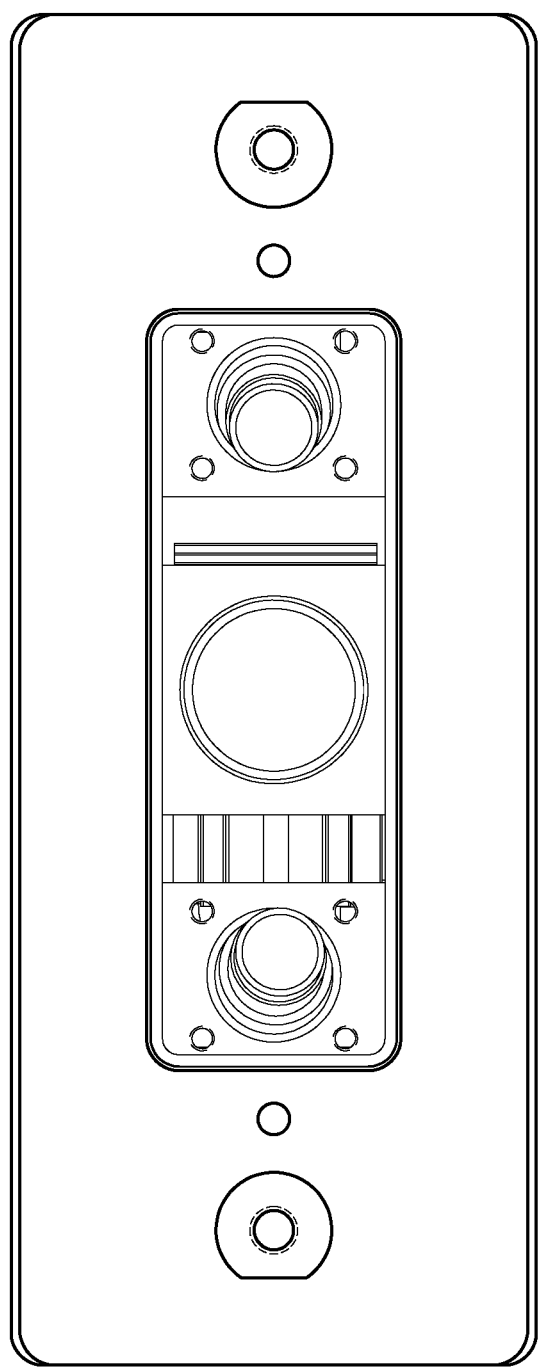
Figure 3D:
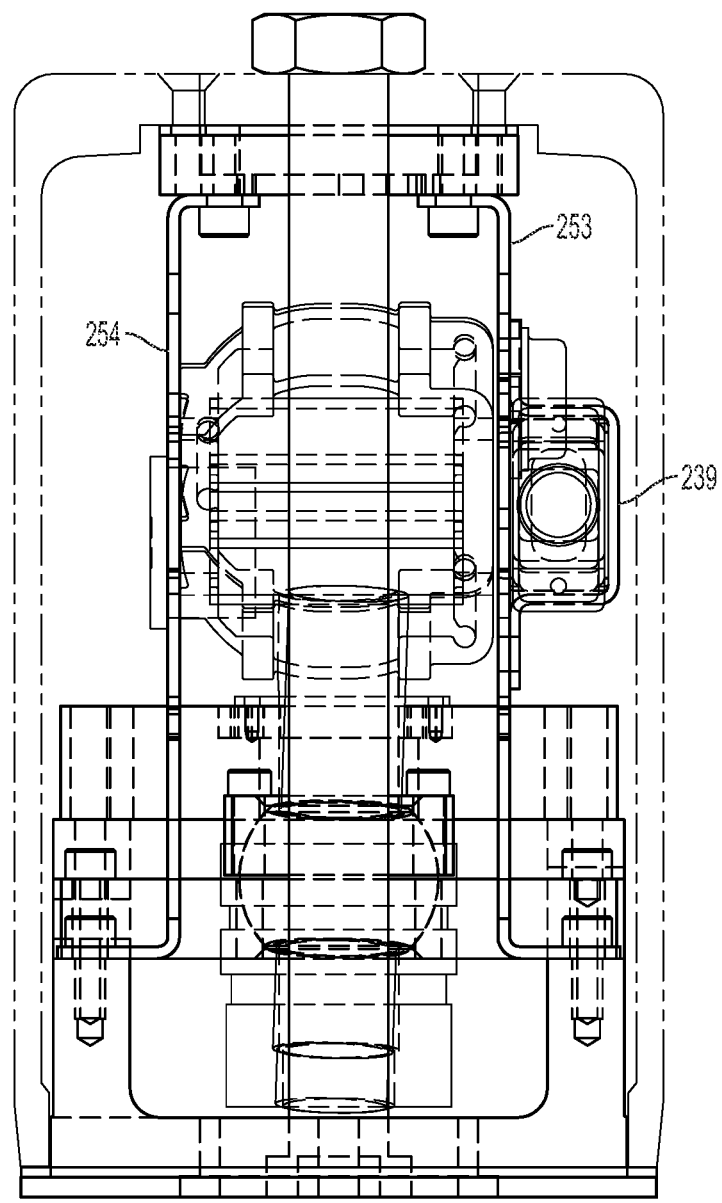
Figure 4A:
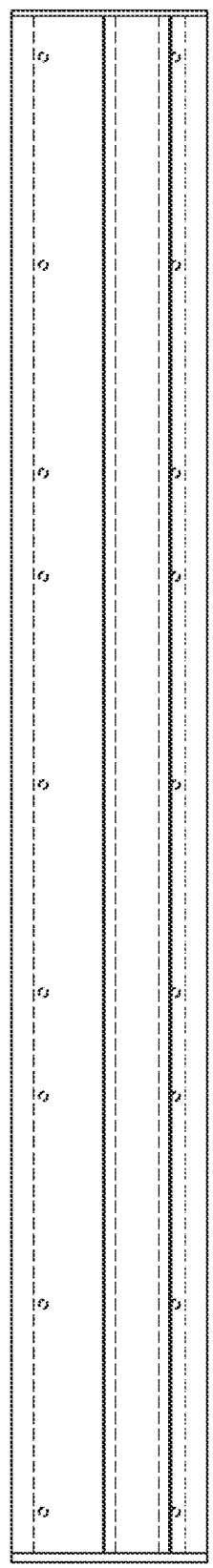
FIGS. 4a-4e illustrate the radiation source of FIG. 2 in accordance with various embodiments.
Figure 4B:
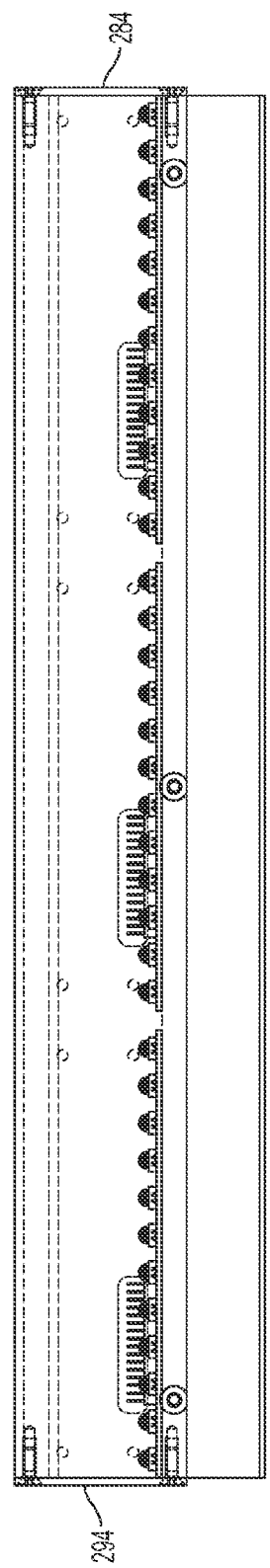
Figure 4C:
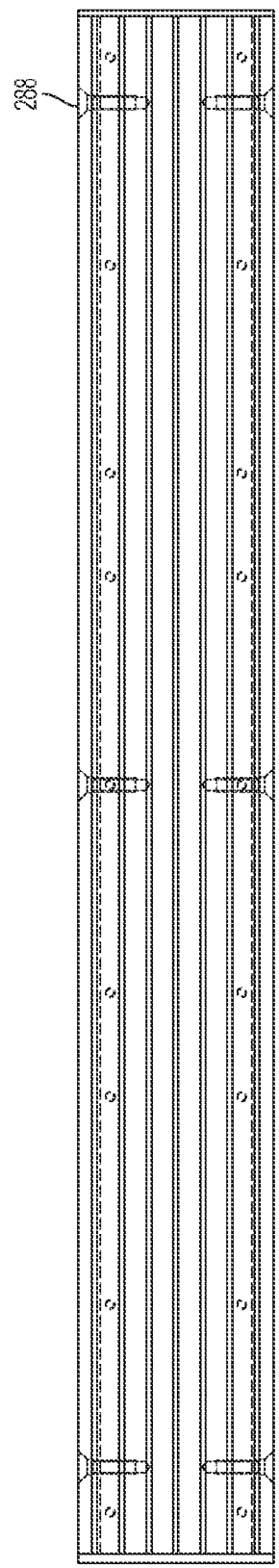
Figure 4D:
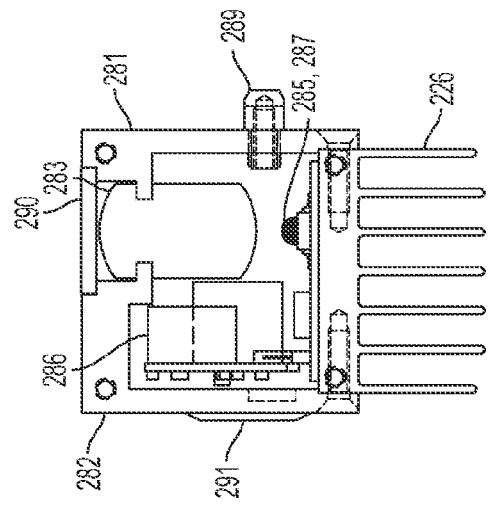
Figure 4E:
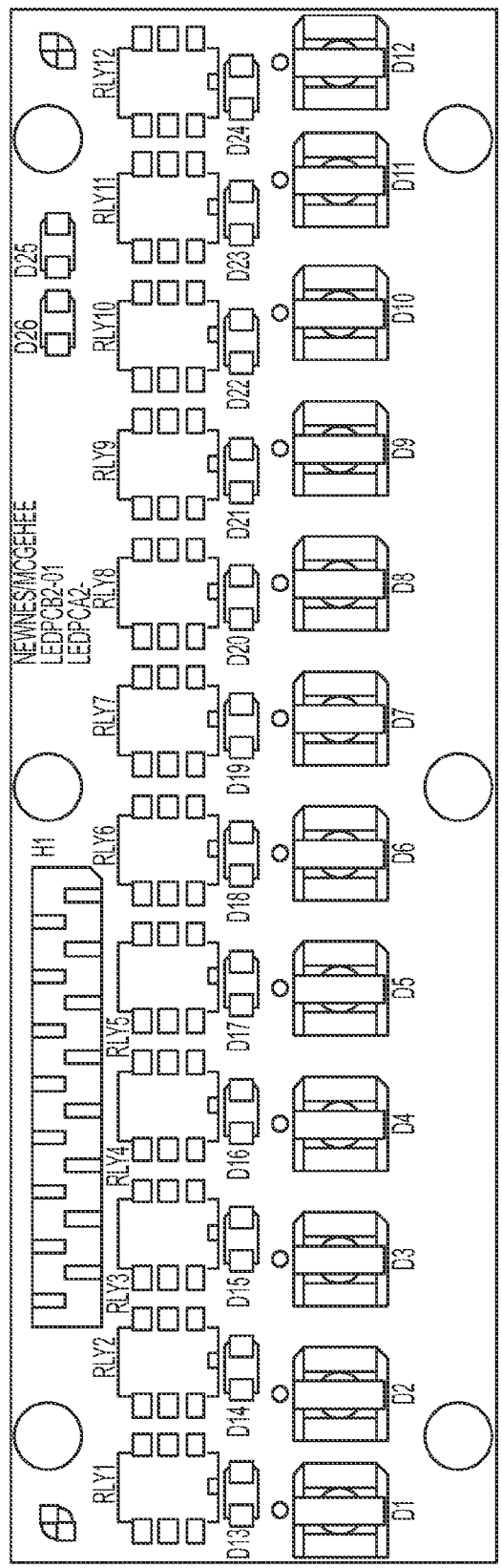

As shown in FIG. 3a, some imaging modules may include one or more optical lasers 260/261. Other imaging modules 212 may lack an integrated optical laser. Optical lasers may be used, for example, to guide repositioning and/or adjustment of imaging module 212, radiation source 216, or the position/speed of a transport surface. Alternatively, optical lasers may be used to induce emission of light from a workpiece. For example, some imaging modules 212 may include one or more radiation sources (e.g. UV light sources) and may lack an external radiation source 216.

Radiation source 216 includes an external linear UV LED light source 285 with a peak wavelength of 365 nm, a 48 VDC power supply, and a heat sink 226. As shown in FIGS. 4a-4e and the accompanying Chart 2 below, radiation source 216 may include additional components, such as a thermostat 292.

CHART 2

| MK | QTY | DESCRIPTION |
|---|---|---|
| 281 | 1 | SIDE MOUNT |
| 282 | 1 | SIDE MOUNT |
| 283 | 1 | FOCAL ROD |
| 226 | 1 | HEATSINK |
| 284 | 1 | END CAP FLAT |
| 285 | 3 | LED LIGHT BAR PCA UV V1R0 |
| 286 | 3 | LED POWER PCA V1R1 |
| 287 | 0.3 | THERMAL CONDUCTIVE PAD 0.5 MM |
| 288 | 10 | FLAT HD MACH SCRW 8-32 X ½ |
| 289 | 2 | INSERT |
| 290 | 1 | CLASS 17.75" X 1" CLEAR 3 MM |
| 291 | 3 | PLUG-RECT BUTTON .75 X 1.5 |
| 292 | 1 | SELCO DISC THERMOSTAT 55C NC |
| 293 | 18 | WASHER #4 NYLON SHOULDER |
| 294 | 1 | END CAP FLAT W/HOLE |
| 295 | 1 | STRAIN RELIEF BUSHING 0.245" |
| 296 | 1 | CONN #14 INSERT 5-PIN |
| 297 | 1 | CONN #14 SHELL CLAMP W/BUSHING |

CHART 2-continued

| MK | QTY | DESCRIPTION |
|---|---|---|
| 298 | 1 | CONN #14 RECP SHELL CIRCULAR |
| 299 | 1 | CABLE 1 PR 18 G SHLD BELD8760 |

Figure 5A:
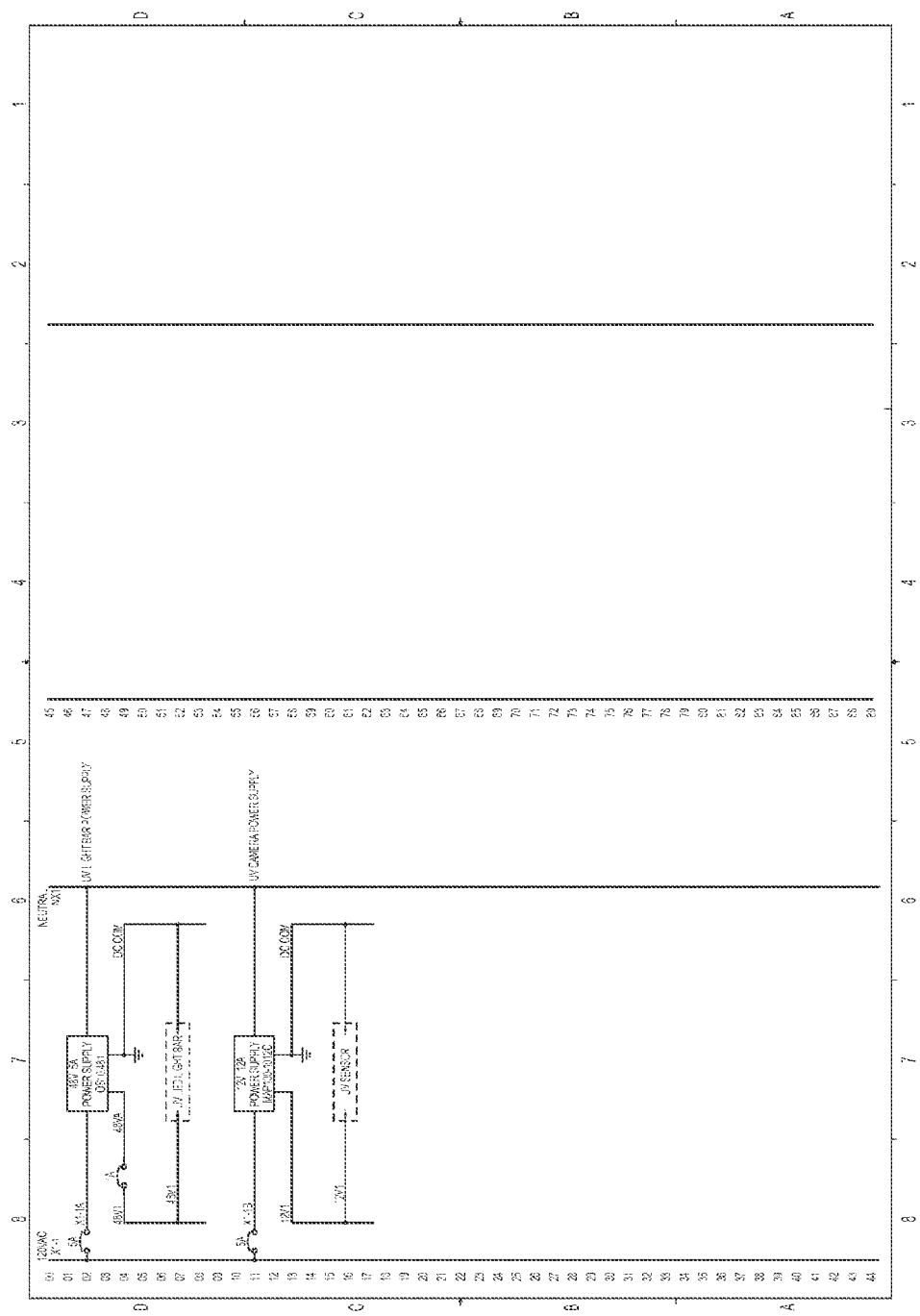
FIGS. 5a and 5b illustrate an electrical schematic of an imaging module and radiation source in accordance with various embodiments.
Figure 5B:
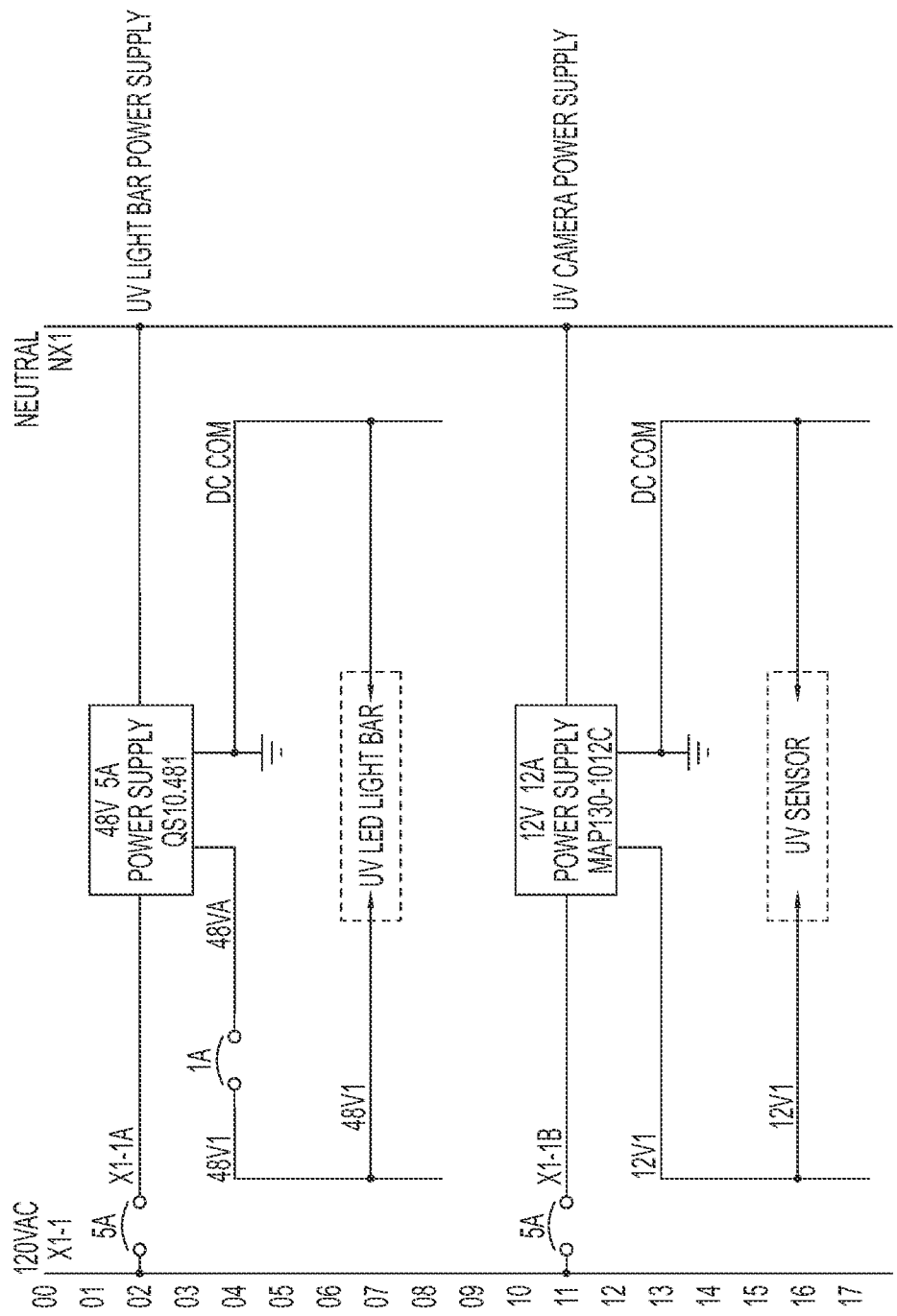

Radiation source 216 is shown mounted to imaging module 212 by mounting assembly 224 (FIG. 2). Radiation source 216 and imaging module 212 may share common circuitry and/or be electrically coupled. FIGS. 5a and 5b illustrate an example of an electrical schematic for imaging module 212 and radiation source 216.

Mounting assembly 224 may include one or more mechanical fasteners configured to fasten radiation source 216 and/or imaging module 212 to another structure or support such as a wall, ceiling, or frame. Mounting assembly 224 may configured to accommodate manual or automatic repositioning of radiation source 216 and/or imaging module 212. For example, imaging module 212 may be pivotally or movably coupled to a first portion of mounting assembly 224, radiation source 216 may be pivotally or movably coupled to a second portion of mounting assembly 224, and a third portion of mounting assembly 224 may be coupled to the first portion, the second portion, and to a wall, ceiling, or frame. Mounting assembly 224 may further include one or more actuators coupled, for example, to a processing module (e.g., processing module 122, FIG. 1). The actuators may be configured to adjust the position and/or angle of the imaging module and/or mounting assembly in response to a command from the processing module. While FIG. 2 shows radiation source 216 positioned at an angle of about 14° from vertical and imaging module 212 at an angle of 2° from vertical, the relative positions of these components may vary as discussed above with reference to FIG. 1.

Any of the above-described systems and/or assemblies may be used to determine a wood species of a workpiece according to various methods. One example of such a method may proceed as follows. First, an imaging module and radiation source may be positioned proximal to a workpiece support, such as a transport. The radiation source may be configured to emit one or more beams of light, such as a line of UV light that extends across the workpiece (i.e. transverse to the direction of transport). The radiation source and imaging module may be positioned such that the field of view of the imaging module intersects the light emitted by the radiation source. The intersection may occur on or above the upper surface of the transport.

As a workpiece is translocated on the transport in the direction of flow, the workpiece is contacted by the emitted light as described above. Pitch within the illuminated portion of the workpiece may absorb energy from the emitted light and reemit energy as visible light, such as visible light in the green spectrum. The imaging module may capture an image of the workpiece, such as a line image corresponding to the illuminated portion. The imaging module may send the captured image to a processing module coupled to the imaging module and/or radiation source.

The processing module may assemble the received images into a full or partial image of the workpiece. The processing module may analyze the assembled image to determine one or more pitch characteristics. The processing module may then determine the wood species of the workpiece based at least on the one or more pitch characteristics. The determination may also be at least partially based on other received data, such as color/tone data, wood grain data, density data, and/or other received data corresponding to a physical characteristic of the workpiece. Such data may be received, for example, from a scanner, a camera, ultrasound, X-ray, or other device. The processing module may further use the image data, assembled image, pitch characteristics, wood species data, or other data to another device (e.g., scanner/optimizer, processor, computer, etc.) to determine sorting, grading, defect detection, or other process, or send the data to another device (e.g., a scanner/optimizer, processor, controller, or computer) for any or all of those purposes.

For example, the processing module may determine a grading system or sorting decision to be applied to a workpiece based on the determination of wood species. As another example, the processing module may send the assembled image of the workpiece and/or the species determination to another processor. One or both processors may integrate the assembled image with another image of the workpiece and analyze the integrated image to detect defects, determine an optimized cutting solution, predict strength/stiffness, assign a grading system to be used, determine a sorting decision, determine an optimized position for the workpiece, adjust a guide element or cutting element of a cutting or wood processing machine, and/or send a command to another component of a lumber processing system in accordance with any of the above determinations, as described above.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A wood species detection method, comprising:
   directing one or more beams of UV radiation onto a piece of wood while the piece of wood is moved by a transport in a direction of flow;
   capturing one or more images of fluorescent light emitted by pitch on/in the piece of wood, the fluorescent light emitted in response to absorption of the UV radiation by the pitch;
   determining one or more pitch characteristics based at least on the one or more images, wherein the one or more pitch characteristics includes pitch content, pitch location, a pattern of pitch deposition, or pitch fluorescence wavelength;
   comparing the one or more pitch characteristics to wood species reference data; and
   identifying or verifying a wood species of the piece of wood based at least on the comparison.

2. The method of claim 1, wherein the one or more images are sequential images of the piece of wood, the method further comprising assembling the sequential images into an image of the piece of wood, wherein the one or more pitch characteristics are determined based at least on the image of the piece of wood.

3. The method of claim 1, wherein the one or more pitch characteristics includes two or more of pitch content, pitch location, pitch deposition pattern, and pitch emission wavelength.

4. The method of claim 1, wherein the wood species reference data includes a signature profile of the wood species of the piece of wood.

5. The method of claim 4, wherein the signature profile includes two or more of pitch content, pitch location, a pattern of pitch deposition, or pitch fluorescence wavelength, and wherein the wood species of the piece of wood includes a plurality of sub-species or varieties of tree.

6. The method of claim 1, wherein directing the one or more beams of UV radiation onto the piece of wood includes emitting the one or more beams of UV radiation from a UV light source that is oriented transverse to the direction of flow.

7. A wood species identification system, comprising:
a UV radiation source positioned to emit a beam of UV radiation onto a piece of wood on a transport as the piece of wood is moved in a flow direction by the transport;
an imaging module positioned to capture one or more images of the piece of wood on the transport, wherein the imaging module is configured to capture the one or more images as one or more images of fluorescent light emitted by pitch on or within the piece of wood, and the fluorescent light is emitted by the pitch in response to absorption of the UV radiation by the pitch; and
a processing module operatively coupled to the imaging module and the UV radiation source, the processing module further including executable instructions operable, upon execution, to
determine one or more pitch characteristics of the piece of wood based at least on the one or more images, wherein the one or more pitch characteristics includes pitch content, pitch location, a pattern of pitch deposition, or pitch fluorescence wavelength,
compare the one or more pitch characteristics to wood species reference data, and
identify or verify a wood species of the piece of wood based at least on the comparison.

8. The wood species identification system of claim 7, wherein the radiation source comprises a plurality of UV LED lights.

9. The wood species identification system of claim 7, wherein the one or more images includes a plurality of sequential images, and the processing module is further configured to assemble the plurality of sequential images into an image of at least part of the piece of wood and to determine the one or more pitch characteristics based on the assembled image.

10. The wood species identification system of claim 8, wherein the UV LED lights are arranged transverse to the flow direction.

11. The wood species identification system of claim 7, wherein the imaging module comprises at least one of a CCD imager or an APS imager.

12. The wood species identification system of claim 7, wherein the imaging module comprises a CMOS imager.

13. The wood species identification system of claim 7, further comprising a mounting assembly, wherein at least one of the radiation source and the imaging module is movably coupled to the mounting assembly.

14. The wood species identification system of claim 13, the mounting assembly further including at least one actuator configured to reposition one or more of the radiation source and the imaging module in response to a command from the processing module.

* * * * *